US011452566B2

(12) United States Patent
Michael et al.

(10) Patent No.: US 11,452,566 B2
(45) Date of Patent: Sep. 27, 2022

(54) PRE-OPERATIVE PLANNING FOR REORIENTATION SURGERY: SURFACE-MODEL-FREE APPROACH USING SIMULATED X-RAYS

(71) Applicant: INTELLIJOINT SURGICAL INC., Kitchener (CA)

(72) Inventors: Justin Aaron Michael, Kitchener (CA); Joseph Arthur Schipper, Kitchener (CA); Andre Novomir Hladio, Waterloo (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 368 days.

(21) Appl. No.: 16/712,266

(22) Filed: Dec. 12, 2019

(65) Prior Publication Data
US 2020/0197096 A1 Jun. 25, 2020

Related U.S. Application Data

(60) Provisional application No. 62/783,597, filed on Dec. 21, 2018.

(51) Int. Cl.
*A61B 34/10* (2016.01)
*A61F 2/32* (2006.01)
(Continued)

(52) U.S. Cl.
CPC .............. *A61B 34/10* (2016.02); *A61F 2/32* (2013.01); *G06T 7/0012* (2013.01); *G06T 7/30* (2017.01);
(Continued)

(58) Field of Classification Search
CPC ...... A61B 2034/102; A61B 2034/2065; A61B 2090/363; A61B 2090/364; A61B 2090/374; A61B 2090/3762; A61B 2090/3966; A61B 34/10; A61F 2/32; A61F 2002/4633; G06T 2207/10124; G06T 7/0012; G06T 7/30; G06T 7/62;
(Continued)

(56) References Cited

U.S. PATENT DOCUMENTS

2013/0094742 A1\* 4/2013 Feilkas .................. A61B 6/584
382/131
2017/0178324 A1\* 6/2017 Saget ........................ G06T 7/33
(Continued)

FOREIGN PATENT DOCUMENTS

WO WO-2013025814 A1 \* 2/2013 ........... A61B 17/155

*Primary Examiner* — Sing-Wai Wu (57) ABSTRACT

Preoperative planning techniques are described such as for hip surgery. Rather than pre-operatively planning by reorienting a model of the boundaries of the acetabulum derived from a 3D medical image, the proposed solution reorients portions of the 3D medical image itself and simulates one or more x-ray images using the reoriented 3D data. Optionally, simulated x-ray(s) of the un-modified CT scan may also be generated for comparison purposes. The user then measures acetabular metrics on the simulated x-ray(s) in order to determine the radiographic outcomes that a given magnitude and direction of reorientation would achieve. By iteratively selecting a reorientation and measuring the simulated x-ray(s), an optimal reorientation plan is determined by the user.

18 Claims, 6 Drawing Sheets

(51) Int. Cl.
*G06T 7/00* (2017.01)
*G06T 7/30* (2017.01)
*G06T 7/62* (2017.01)
*G16H 30/40* (2018.01)
*G16H 50/50* (2018.01)
*A61B 34/20* (2016.01)
*A61B 90/00* (2016.01)
*G16H 30/20* (2018.01)
*G16H 15/00* (2018.01)
*A61F 2/46* (2006.01)

(52) U.S. Cl.
CPC .............. *G06T 7/62* (2017.01); *G16H 15/00* (2018.01); *G16H 30/20* (2018.01); *G16H 30/40* (2018.01); *G16H 50/50* (2018.01); *A61B 2034/2065* (2016.02); *A61B 2090/363* (2016.02); *A61B 2090/364* (2016.02); *A61B 2090/374* (2016.02); *A61B 2090/3762* (2016.02); *A61F 2002/4633* (2013.01); *G06T 2207/10124* (2013.01)

(58) Field of Classification Search
CPC ........ G16H 15/00; G16H 20/40; G16H 30/20; G16H 30/40; G16H 50/50
See application file for complete search history.

(56) References Cited

U.S. PATENT DOCUMENTS

2018/0140309 A1* 5/2018 Fouts .................... G06T 7/0012
2019/0231434 A1* 8/2019 Lambers ................ A61B 34/10

\* cited by examiner

PRE-OPERATIVE PLANNING FOR REORIENTATION SURGERY: SURFACE-MODEL-FREE APPROACH USING SIMULATED X-RAYS

FIELD

The present disclosure relates to computing systems and methods more particularly to pre-operative planning for reorientation surgery using simulated x-rays in a surface-model-free approach.

BACKGROUND

Peri-acetabular osteotomy (PAO) is a surgical technique to treat hip dysplasia, a disorder in which the acetabulum is too shallow, resulting in poor biomechanics of the hip. PAO involves cutting the pelvis to free a bone fragment containing the acetabulum, rotating the freed bone fragment, and re-attaching it to the pelvis in order to improve the biomechanics of the patient's hip. Clinical metrics of acetabular shape and orientation are typically measured using x-ray images based on anatomic landmarks and/or radiographic features, with those same metrics used to define desired surgical outcomes.

Existing software tools to pre-operatively plan the direction and magnitude of acetabular rotation use a 3D medical image, typically a CT image, and a boundary-based simulation. A 3D surface model (boundary) of the acetabulum is generated from the 3D medical image using segmentation or statistical modelling techniques such as statistical shape models. The acetabulum is then virtually 'cut' from the surface model and reoriented, allowing metrics typically assessed in x-ray images to be calculated from the acetabulum's shape and orientation. Planning consists of iteratively selecting the rotation of the fragment and determining the resulting acetabular metrics until an optimal rotation is found.

While the above approach to planning software is effective, it requires the intermediate step of defining the boundaries of the pelvis and/or acetabulum. Requiring the boundaries of the acetabulum to be defined adds considerable burden to its development and/or use. The process of 3D segmentation is tedious and time consuming to perform manually, and algorithmic segmentation techniques are complex to develop and validate. Statistical modelling techniques are also complex to develop and additionally require large numbers of labelled data sets. The definition of acetabular boundaries, typically in the form of a surface model, therefore adds considerable cost and complexity to the development and/or use of pre-operative planning software using a boundary-based approach.

SUMMARY

Preoperative planning techniques are described such as for hip surgery. Rather than pre-operatively planning by reorienting a model of the boundaries of the acetabulum derived from a 3D medical image, the proposed solution reorients portions of the 3D medical image itself and simulates one or more x-ray images using the reoriented 3D data. Optionally, simulated x-ray(s) of the un-modified CT scan may also be generated for comparison purposes. The user then measures acetabular metrics on the simulated x-ray(s) in order to determine the radiographic outcomes that a given magnitude and direction of reorientation would achieve. By iteratively selecting a reorientation and measuring the simulated x-ray(s), an optimal reorientation plan is determined by the user.

There is provided a computer implemented method for performance by a processing unit of a computing device. The method comprises: accessing a first volumetric data set of a medical image comprising anatomic structures; determining a volumetric region with respect to the first volumetric data set of an anatomic structure to be reoriented; computing a first measurement of a parameter of the anatomic structure; receiving a positional change of the volumetric region with respect to the first volumetric data set; generating a second volumetric data set corresponding to the first volumetric data set and responsive to the positional change to the volumetric region; generating a change image comprising a digitally reconstructed radiograph (DRR) from the second volumetric data set; and providing the change image for display.

In the method, determining the volumetric region may comprise receiving user input defining anatomic features as displayed on at least one slice view of the volumetric data set.

The method may comprise generating a baseline image comprising the DRR from the first volumetric data set without regard to the positional change to the volumetric region; and providing the baseline image for display. The first measurement of a parameter may be computed based on user input defining anatomic landmarks on the baseline image.

The first measurement of a parameter may be computed based on user input defining anatomic landmarks relative to the first volumetric data set.

Computing the first measurement may compute the first measurement of a plurality of parameters.

Computing the first measurement of the parameter may comprise computing one of: i) a lateral center edge angle (LCEA); ii) an anterior center edge angle (ACEA); and iii) both the LCEA and the ACEA.

Positional change of the volumetric region may comprise any one of:
a desired anteversion and/or inclination angle of an acetabulum;
a desired LCEA and/or ACEA;
a desired hip center of rotation location; and
a value determined from a user manipulation receive via a user interface of the volumetric region using a computer input device in at least one slice view of the volumetric data set, wherein the at least one slice view is displayed.

The method may further comprise determining a second measurement of one or more parameters of the anatomic structure in the second volumetric data set. The second measurement of one or more parameters may be based on a user input defining anatomic landmarks on either: a DRR of the second volumetric data set; and a DRR of the first volumetric data set responsive to the positional change of the volumetric region. The method may comprise determining the positional change to optimize the second measurement of the one or more parameters relative to respective desired values for the one or more parameters. Determining the positional change may comprise one of: determining the positional change automatically via an iterative algorithm; receiving user input and presenting updated measurements of the one or more parameters to guide an iterative process.

The method may further comprise generating navigation target parameters corresponding to the positional change in a registration coordinate frame. The method may comprise providing (such as communicating and/or transmitting) the navigation target parameters to a surgical navigation system. The navigation target parameters may comprise angles of inclination and anteversion of a hip joint.

The computing device may comprise a server (though other computing devices and form factors thereof may be used). Input representing the positional change to the volumetric region may be received at the server from a client computing device.

The DRR from the second volumetric data set is determined by updating a DRR from the first volumetric data set in only the region corresponding to the volumetric region for which the positional change is received.

The method may comprise receiving a second or subsequent input defining a second or subsequent positional change and performing the steps of:

one of: a) updating the second volumetric data set responsive to the second or subsequent positional change; and b) generating a further volumetric data set responsive to the second or subsequent positional change;

generating an updated change image comprising a digitally reconstructed radiograph (DRR) from one of the second volumetric data set as updated and the further volumetric data set; and providing the updated change image;

thereby to iteratively perform reorientation of the anatomic structure.

The anatomic structures may comprise a hip joint.

There is provided a computing device comprising a processing unit and a storage unit coupled thereto, the storage unit storing instructions, which when executed by the processing unit, configure the computing device to perform a method in accordance with the computer method aspect herein.

There is provided a computing program product comprising a non-transient storage unit storing instructions, which when executed by a processing unit of a computing device, configure the computing device to perform a method in accordance with the computer method aspect herein.

DETAILED DESCRIPTION

The proposal herein comprises an alternative pre-operative planning process that does not require the boundaries of the pelvis or acetabulum to be defined and thus avoids the associated cost and complexity.

Rather than pre-operatively planning by reorienting a model of the boundaries of the acetabulum derived from a 3D medical image, the proposed solution reorients portions of the 3D medical image itself and simulates one or more x-ray images using the reoriented 3D data. Optionally, simulated x-ray(s) of the un-modified CT scan may also be generated for comparison purposes. The user then measures acetabular metrics on the simulated x-ray(s) in order to determine the radiographic outcomes that a given magnitude and direction of reorientation would achieve. By iteratively selecting a reorientation and measuring the simulated x-ray(s), an optimal reorientation plan is determined by the user.

Pre-planning techniques described herein may be performed from initial 3D medical images, such as one or more of:

3D medical images (CT, MRI, ultrasound, etc.) as they are traditionally captured and presented ("unprocessed");

3D medical images that have been subsequently processed, filtered, or otherwise enhanced for clarity (e.g. noise reduction, artifact removal, contrast enhancement, cropping, etc.);

Estimates of 3D medical images in one modality that are based on medical images in a different modality (e.g. taking a patient MRI and synthetically generating an estimate of what a CT scan of the same patient would look like); and Many surface models of regular size and shape, each with an associated material property. E.g. conversion of every voxel in a CT scan into a rectangular surface model the same size and shape of the original voxel with the intensity of that voxel associated with it as a material property. Effectively, 3D images masquerading as surface models.

3D images typically comprise data defined as volumetric datasets.

To generate a simulated x-ray of the reoriented 3D data, the user marks the center of the affected hip and a region of interest around the hip in the CT image that includes all of the acetabulum (e.g. a sphere larger than the acetabulum). This region of interest is then rotated in a user selected magnitude and direction and an x-ray image of the modified CT image is simulated. Soft tissue has only a very small impact on the simulated x-ray image compared to the surrounding bone. As a result, even though a region of both bone and soft tissue are rotated in the CT, the resulting simulated x-ray is dominated by the movement of bony anatomy, despite not knowing the exact shape and position of the bony anatomy that was rotated. Relevant radiographic metrics can then be measured by the user on the simulated x-ray without requiring the boundaries of the pelvis or acetabulum to be defined.

A simulated x-ray image generated from a 3D CT image is known as a digitally reconstructed radiograph (DRR). The DRR technique for simulating x-rays from 3D CT images leverages the close relationship between CT and x-ray images. The intensity of a voxel in CT data represents an estimate of the x-ray attenuation of the material inside that voxel, making it possible to model the attenuation of a simulated x-ray as it passes through the voxels of a CT image. While DRRs are an established technique, more common applications for DRRs are in planning radiation therapy and facilitating the registration (alignment) of 2D x-rays with 3D CTs.

The properties of DRR's allow the process of simulating an x-ray of a modified CT image to be conducted in at least two ways. The first approach is to rotate the defined region of interest in the original CT image, rejoin the rotated region of interest with the remainder of the image to form a second CT image, and simulate a DRR of the second CT image.

The second approach is to separately simulate a DRR of only the rotated region of interest and a DRR of only the remainder of the original CT image and leverage the multiplicative properties of x-ray attenuation to combine the two DRR's. The intensity of a given pixel in a DRR is mapped from the modelled transmission of x-ray radiation traveling from a simulated x-ray source to the location of that pixel on a simulated detector. This transmission is expressed as a value between 0 and 1, describing the proportion of the original x-ray radiation transmitted. The total transmission resulting from both components of the CT image at a given pixel may be found by multiplying the transmission values at that pixel for each individual CT component. By repeating this process for each pixel and mapping the total transmission to pixel intensity, the two DRR's may be combined.

With the exception of any differences in rounding, approximation or other numerical errors, the two approaches described above are mathematically equivalent and can be used interchangeably.

An example application of the proposed approach in accordance with an example of the teaching herein is described below. A pre-operative reorientation plan is generated using the following steps.

Figure 1A:
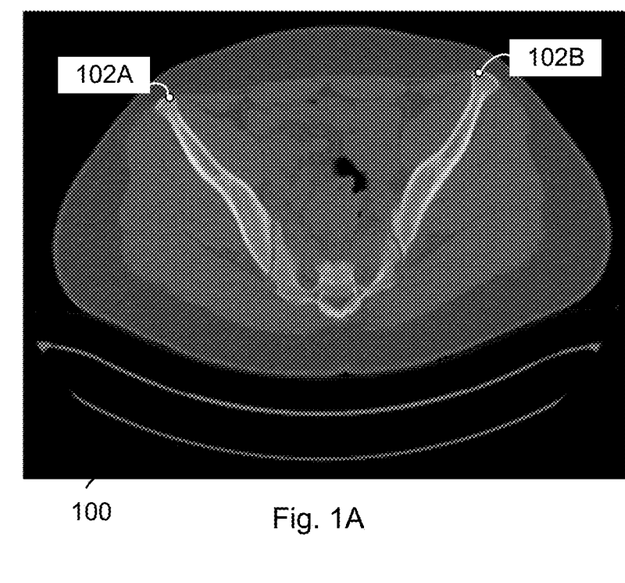
FIGS. 1A and 1B are before and after images from a volumetric data set with annotation for an alignment operation of planning and which images may be presented by an interface of a computing device and/or computing system configured to perform planning in accordance with an embodiment
Figure 1B:
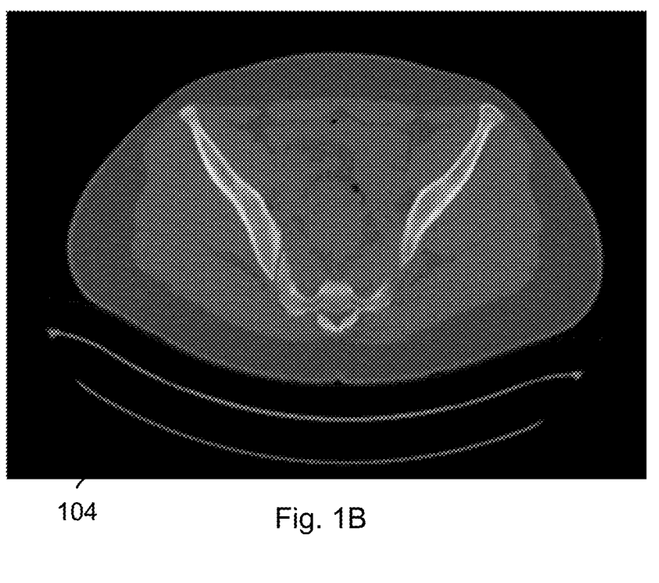

Orient the Patient CT Using Manual Identification of Bony Landmarks:

In a CT image 100 of FIG. 1A, a user manually identifies two bony landmarks 102A and 102B and the CT image is rotated, aligning those landmarks horizontally as CT image 104 (FIG. 1B, right) to correct for patient roll.

Figure 2A:
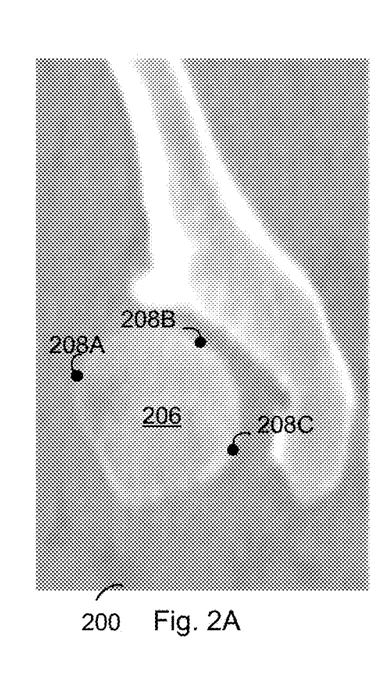
FIGS. 2A, 2B and 2C are images (from a volumetric data set) with annotation that may be presented by an interface of a computing device and/or computing system configured to perform planning in accordance with an embodiment.
Figure 2B:
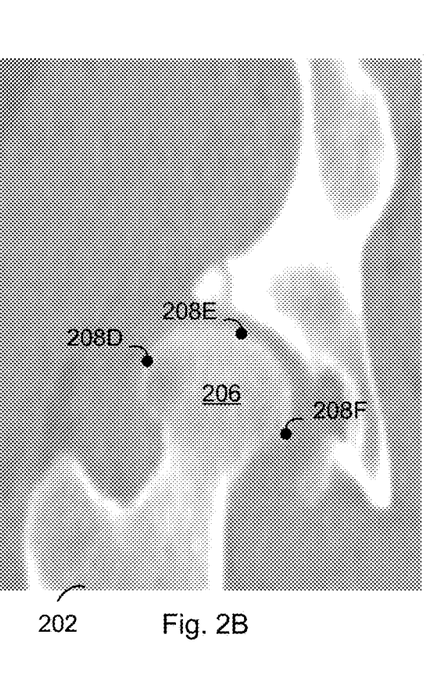
Figure 2C:
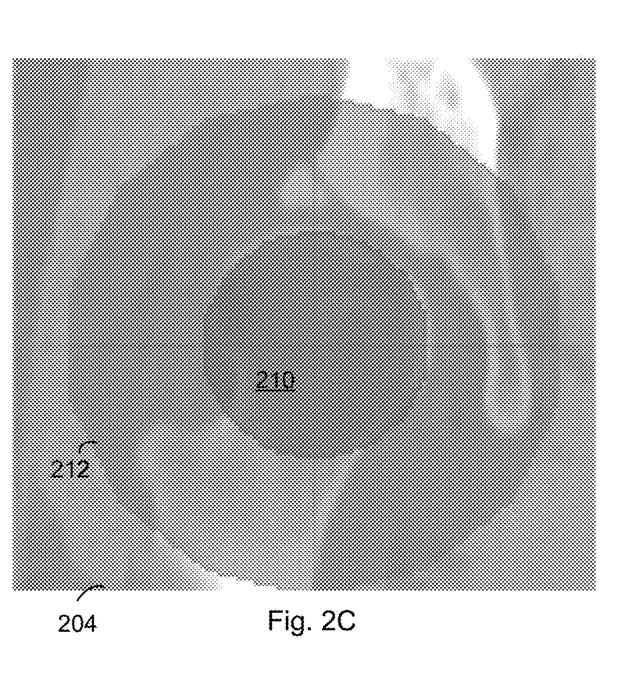

Manually Define Hip Center and Surrounding Area in CT:

With reference to FIGS. 2A-2C showing images 200, 202 and 204, the user places at least four points on the femoral head 206 in the CT image (six points (208A, 208B, 208C, 208D, 208E and 208F) shown). A sphere 210 is fit (see FIG. 2C) to the selected points and its radius expanded to define a region of interest 212 for reorientation.

Figure 3A:
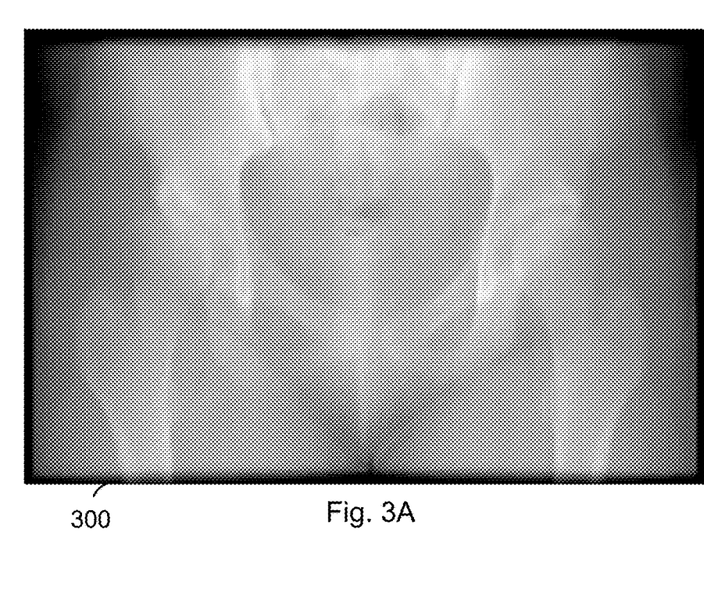
FIGS. 3A and 3B are before and after radiographs, which may be presented by an interface of a computing device and/or computing system configured to perform planning in accordance with an embodiment.
Figure 3B:
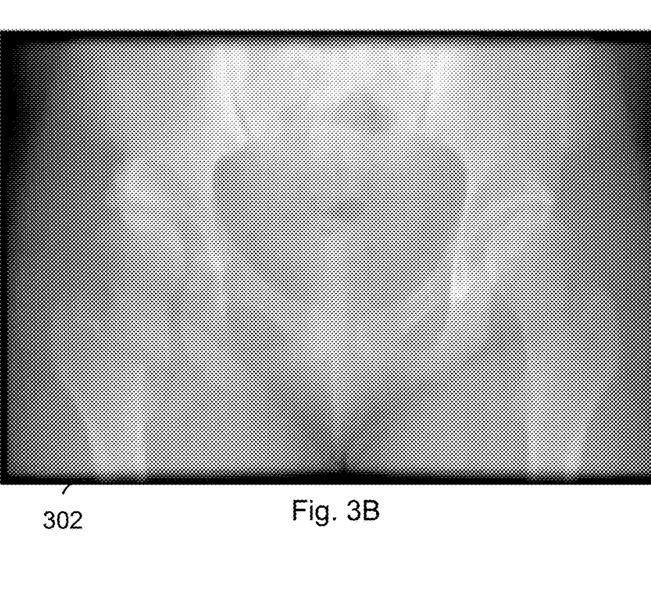

Generate Simulated X-Rays Based on an Estimated Reorientation:

The user selects a reorientation that is applied to the region of interest for reorientation (inner circle in FIG. 2C, right). With reference to FIGS. 3A and 3B, simulated x-rays 300 and 302 are generated from the CT before (300) and after simulated reorientation (302).

Figure 4:
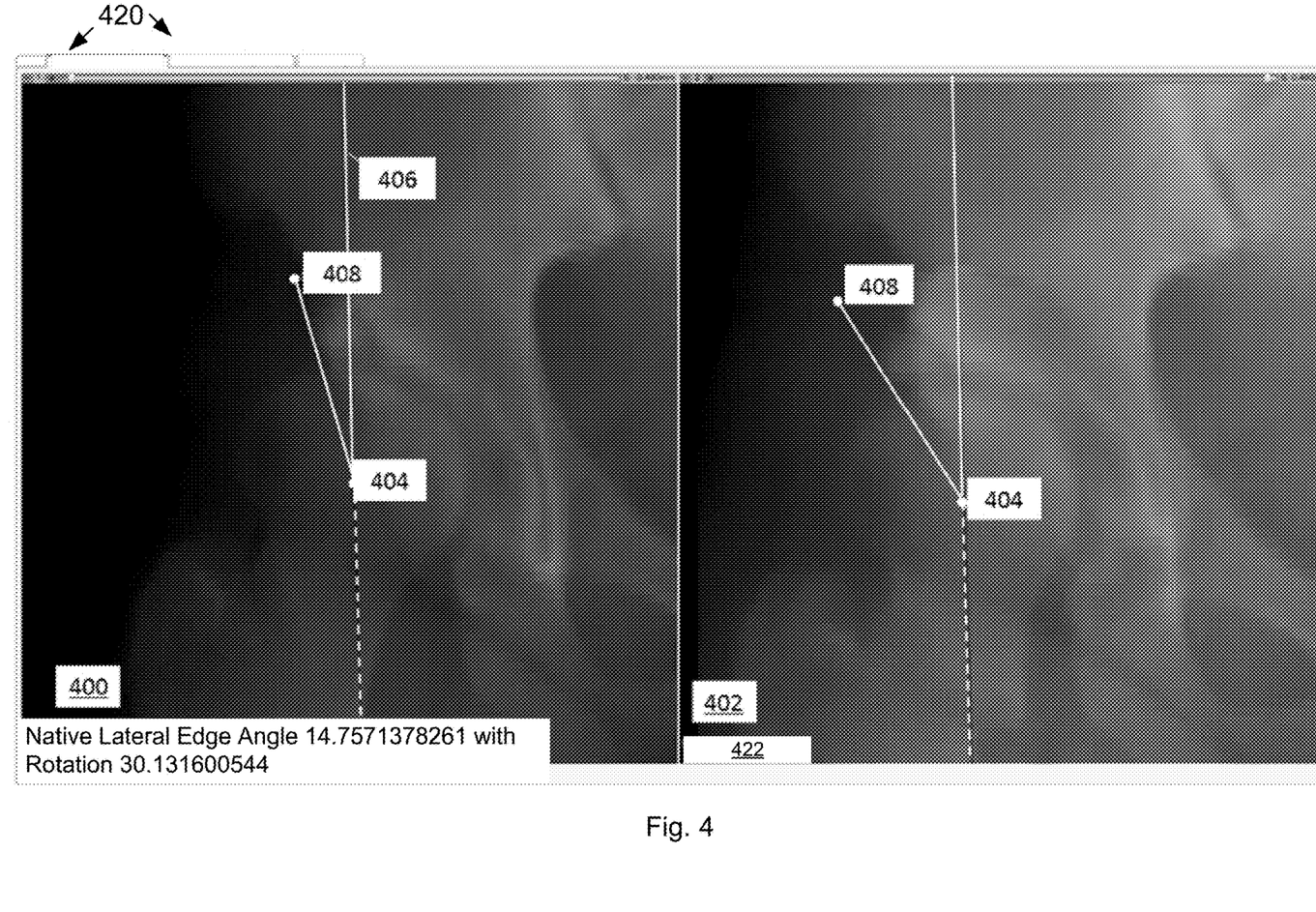
FIG. 4 is a screen shot of a planning interface provided by a computing device and/or computing system in accordance with an embodiment.

Manually Measure Radiographic Parameters in the Simulated X-Rays:

FIG. 4 shows a screen shot of a GUI presenting annotations on digitally reconstructed radiographs 400 and 402 showing before radiograph 400 and after virtual reorientation radiograph 402 of a spherical region of interest of the patient's right hip in CT.

The hip center 404, as defined by the center of the region of interest for reorientation, and the vertical axis 406 of the patient are projected onto the simulated images. The user interactively selects the remaining landmarks on the image 400 of FIG. 4 in order to calculate the desired radiographic metric(s). Points 408 and 404 indicate the lateral edge of the acetabulum 408 (Sourcil (R)) and the projected hip center 404. The angle made by those two points and the projection of the patient's vertical axis 406 (white line for the angle determination and dashed line otherwise) defines the lateral center edge angle, shown in the bottom-left corner to be approximately 15 and 30 degrees, respectively, before and after virtual reorientation. (FIG. 4B contains an artifact in the reoriented DRR (right) that appears to rotate a portion of the femur, even though only the acetabulum would be rotated in a PAO procedure. However, most relevant radiographic metrics are made using only landmarks of the acetabulum and are thus unaffected by this artifact.) The vertical axis and hip center are the same in both images. The hip center and the patient's vertical axis may be defined relative to the CT data and projected onto the simulated x-ray. The lateral edge of the acetabulum may be manually marked by a user on the simulated x-ray. However, marking all landmarks on the simulated x-ray is also possible. In an upper left corner there a tabs 420 with which to select various views and/or functions, including Drr, Lateral Edge Angle, Anterior Centre Edge Angle and Tonnis Angle. Various labels 422 (e.g. file names) may be displayed.

Operations to generate simulated x-rays based on an estimated reorientation: and manually measure radiographic parameters in the simulated x-rays: may be repeated until a desired outcomes are achieved.

Figure 5:
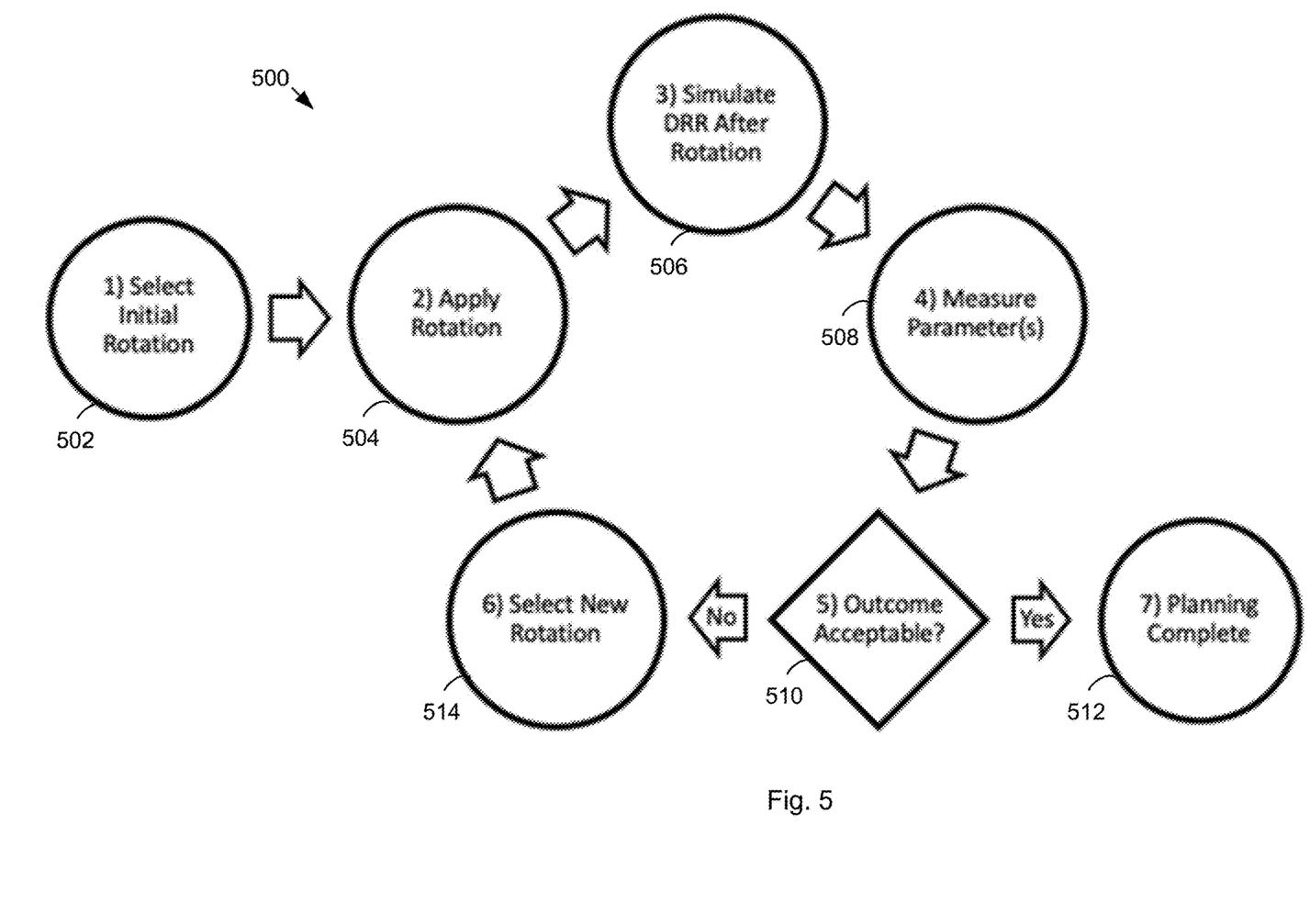
FIG. 5 is a flow chart of operations of a method aspect in accordance with an embodiment.

The user iteratively reselects the rotation applied to the region of interest and re-measures the resulting DRR until an acceptable outcome is achieved. FIG. 5 is a flow chart of operations 500 illustrating iterative optimization of the planned rotation to achieve a desired outcome. An estimate of the desired rotation provides a starting point for the process and the cycle is iteratively repeated until planned rotation until an acceptable outcome is achieved. Aligning the image and defining the region of interest does not need to be repeated. The flow chart illustrates user interaction with a GUI or other interface of a computing device configured to perform planning operations, presenting various images as described, receiving input and defining planning related data as described such as above with reference to FIGS. 1-4. Various operations of the computing device are not shown in FIG. 5 but will be understood. At 502 input is received to select an initial rotation. It will be understood that an interface is presented to receive the input. At 504, a rotation is applied. At 506, DRR is simulated after the rotation. Parameters are measured at 508. If an acceptable outcome is achieved (decision point at 510), via a Yes branch to 512, planning is complete. Otherwise via No branch to 514, a new rotation is selected and operations 504-510 are repeated.

While the above description and the FIGS. describe and show use of modified CT images and DRRs to assist the user in planning PAO procedures, the scope may be increased by the following extensions:

The combination of CT modification and DRRs could be applied to any reorientation procedure where the structure of interest is radiopaque relative to its surroundings, such as bone, or a metal and/or ceramic implant. A selection of procedures for which this solution may be applicable are described in Table 1.

Simulation of the final position of a structure that is removed and replaced, such as an implant that is replaced with a new implant of the same model, could be simulated as a repositioning of the original implant. Thus, procedures that replace a structure with a reoriented version of the same structure could also be planned using this technique.

Research has been published on the generation of DRRs from MRI images, suggesting the solution can also be used when planning with 3D imaging modalities other than CT if combined with a suitable estimation technique for that modality (Ramsey et al, *Clinical application of digitally-reconstructed radiographs generated from magnetic resonance imaging for intracranial lesions*, Int't Journal of Radiation Oncology, Vol. 45, Iss. 3, pp. 797-802).

Simulation of simultaneous rotation and translation of the structure to be reoriented may be performed, rather than rotation only. Translation only may be performed.

Portions of the iterative operations of optimizing the planned reorientation, described with reference to FIG. 5, may be fully automated to further streamline the planning process. While steps 1, 4, 5 and 6 are performed by the computer in response to input (e.g. user input) in a workflow described above, it is possible to further automate some or all of these steps using software. Furthermore, any of these steps can be automated independently, regardless of whether other steps are performed wholly automatically or responsive to user input.

TABLE 1

Proposed reorientation procedures where the structure of interest is radiopaque

| Procedure | Description | Radiopaque Structure |
|---|---|---|
| Peri-Acetabular Osteotomy (PAO) | The acetabulum of the hip is cut from the pelvis, reoriented and re-attached | Acetabulum (bone) |
| Bone-Modifying Osteotomies (e.g. extended trochanteric osteotomy, high tibial osteotomy) | A long bone (e.g. femur, tibia) is cut and reattached at a different angle. | Fragments of femur, tibia, etc. (bone) |
| Implant Revision | A prior implant is repositioned, or removed and replaced with an implant of similar size and shape. | Implant (metal and/or ceramic) |

PAO Planning

In addition to PAO planning techniques that use a segmentation of the pelvis, discussed in Competing Solutions below, research has been published on planning using segmentation of only the acetabular rim rather than the entire surface of the bone. (Liu L., Ecker T., Schumann S., Siebenrock K., Nolte L., Zheng G. (2014) *Computer Assisted Planning and Navigation of Periacetabular Osteotomy with Range of Motion Optimization*. In: Golland P., Hata N., Barillot C., Hornegger J., Howe R. (eds) *Medical Image Computing and Computer-Assisted Intervention—MICCAI 2014. MICCAI 2014. Lecture Notes in Computer Science*, vol 8674. Springer, Cham). The acetabular rim describes a particular transition region on the surface of the acetabulum. The acetabular therefore represents a partial boundary of the acetabulum and similarity requires considerable cost and complexity in order to define. The proposed reorientation techniques herein may be used in this planning scenario as well.

Additionally, in many of the segmentation-based techniques, the pelvic cuts are modelled using a sphere centered on the hip, suggesting that the use of a coarsely defined region of the pelvis has been used previously to model the fragment to be reoriented. (Albers et al, *Preoperative planning for redirective, periacetabular osteotomies*, J. Hip Preserv Surg., 2017 Dec. 4(4): 278-288). However, those approaches use the coarsely defined region to crop the boundaries of the pelvis rather than 3D image data.

Digitally Reconstructed Radiographs (DRRs)

DRRs are a well-established simulation technique, most frequently applied in external beam radiotherapy for treatment planning and to verify patient positioning. The use of DRRs in patient positioning may be referred to as a reconstruction of the "Beam's eye view", an imaging technique used in radiation therapy for external beam radiation therapy treatments.

In addition to the generation of DRRs for simulating radiation therapy, DRRs have also been applied to the registration of X-ray images to CT images. Open source software to generate DRRs from CTs has been published and was used in our instantiation of the solution (available from Plastimatch at pastimatch.org/drr.html).

Manipulation of 3D Medical Images

Software to crop, spatially transform or otherwise modify medical image data is well described and widely distributed, for instance as part of a freely available open source project. (3D Slicer available from Brigham and Women's Hospital, Inc. at slicer.org).

Competing Solutions

As described previously, commercial orthopedic pre-operative planning solutions for the hip commonly provide computer assisted planning and simulation based on 3D surface models of the pelvis, or a sub-region of the pelvis, generated from CT or MRI data. These surface models are generated from either segmentation or model-based techniques that incorporate shape information from previously analyzed patients (e.g. statistical shape models). Examples of commercial solutions for pre-operative planning of hip surgery include Clinical Graphics (from Zimmer Biomet, Delft Netherlands and at clinicalgraphics.com) and Corin OPS™ (from Corin, Cirencester Gloucestershire, UK and at coringroup.com/uk/solutions/optimized-positioning-system-ops/). Similar strategies have also been described in academic research. (Mayman et al, *The Kingston Periacetabular Osteotomy Utilizing Computer Enhancement: A New Technique*, J. Computer Aided Surgery, 2002 Vol. 7, Iss. 3 pp. 179-186).

At least one commercial orthopedic planning product, TraumaCad™ (from Brainlab, Munich, Germany and at traumacad.com), is based on x-ray images rather than CT images. In planning, TraumaCad allows the user to simulate the repositioning of anatomy resulting from a chosen implant by repositioning a portion of the x-ray image. For example, a portion of the x-ray image containing the femur may be translated downwards, towards the patient's feet, to simulate a lengthened leg. This is similar to the proposed solution in that it applies a spatial transformation to a portion of a medical image as part of the pre-operative planning process. It is different from the proposed solution in that,
1) the modification of the medical image data is used for visualization purposes only and does not contribute to anatomic measurements;
2) there is no subsequent synthesis or simulation (e.g. DRR) of the modified medical image after the spatial transformation is applied, and
3) the transformation is limited to translation or rotation in 2D only, rather than 3D.

Computer Implementation

The solution herein may be implemented as a computer method, a computing device, a computer program product or other patent eligible subject matter. In one example, there is provided a computing device comprising a processing unit and a storage unit coupled thereto. The storage unit stores instructions (e.g. software components), which when executed by the processing unit configures the operation of the computing device. The computing device may be so configured to perform a method comprising:

a. accessing a first volumetric data set of a medical image comprising anatomic structures;

b. determining a volumetric region of an anatomic structure to be reoriented;
c. computing a first parameter of the anatomic structure (e.g. initial lateral center edge angle);
d. receiving input representing a positional change of the volumetric region with respect to the first volumetric data set;
e. generating a second volumetric data set corresponding to the first volumetric data set and the positional change to the volumetric region;
f. generating a change image comprising a digitally reconstructed radiograph (DRR) from the second volumetric data set; and
g. providing the change image for display.

The storage unit may be a non-transitory hardware and/or firmware component such as various types of memory, various types of disks, etc.

Figure 6:
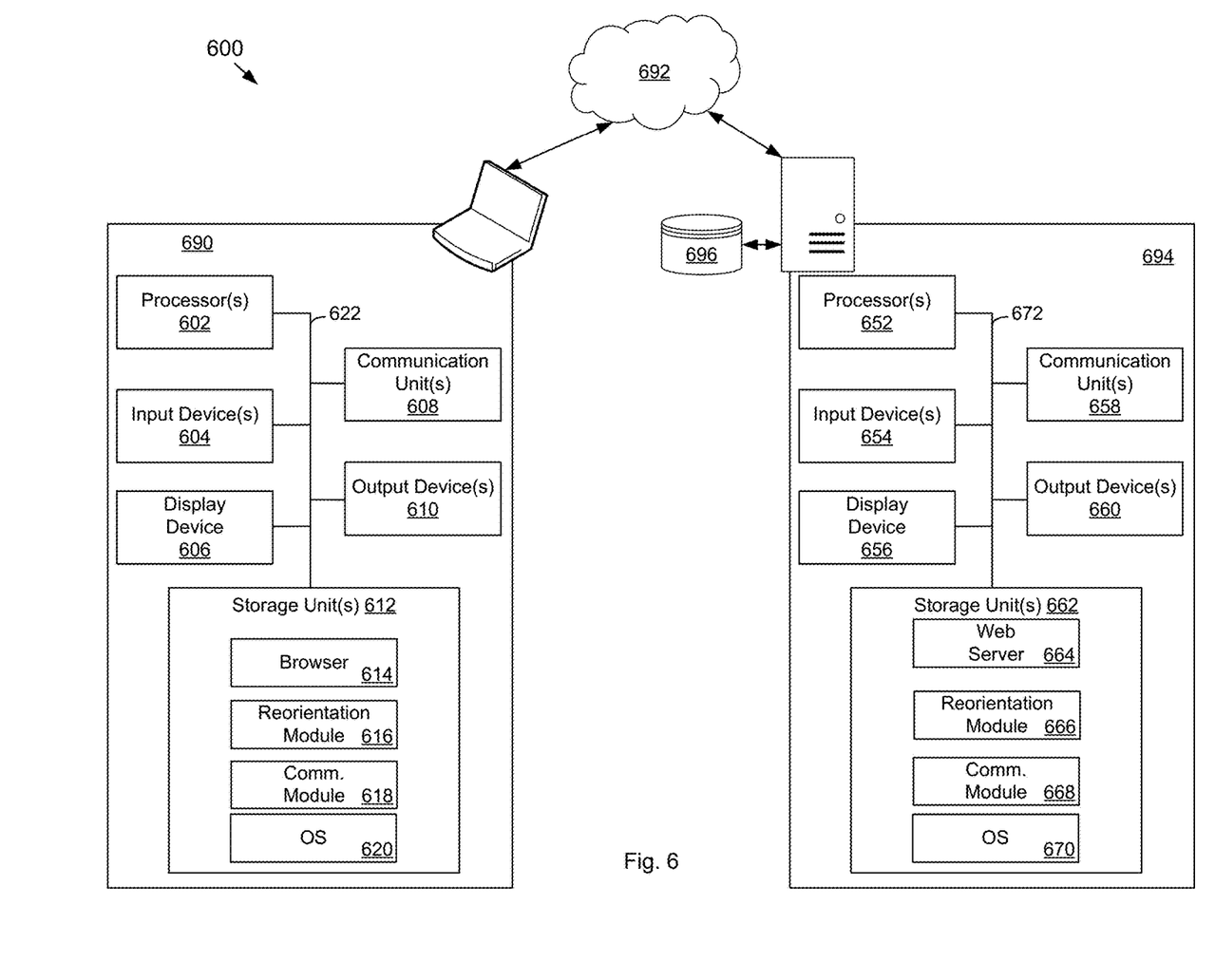
FIG. 6 is a block diagram of a computing system configured for planning in accordance with an embodiment.

In one example, the computing device may be a server such as a web server. A browser based paradigm may be used. Other paradigms may be used. FIG. 6 shows an example computer network system 600 comprising a client computing device 690 communication via a network 692 with a web server 694 having a data store 696.

Client computing device 690 comprises processor(s) 602, input device(s) 604, a display device 606, communication unit(s) 608 and output device(s) 610. Also provided are storage unit(s) 612. Storage units 612 store various software modules/components including a browser 614, reorientation module 616 (for browser 614), communication module 618 and operating system 620. Components of client computing device 690 may be connected via various bus or other internal communication components 622.

Server 694 comprises processor(s) 652, input device(s) 654, a display device 656 (optional), communication unit(s) 658 and output device(s) 660. Also provided are storage unit(s) 662. Storage units 662 store various software modules/components including web server components 664, reorientation module 666 (server side components for reorientation module 616), communication module 668 and operating system 670. Components of server computing device 694 may be connected via various bus or other internal communication components 672. It is apparent that the communication network system 600 and the computing devices 690 and 694 are simplified.

Data store 696 may store browser based application components (e.g. reorientation module 616) to serve to the browser of client computing device 690 as well as server side components (reorientation module 666) that is invocable by input received from the client computing device 690. Data store 696 may store CT or other volumetric data of patient anatomy. Reorientation module 616 may configure client device 690 with a user interface, (e.g. a Graphical User Interface (GUI) with or without voice capabilities) to perform preoperative planning, reorienting CT or other volumetric data and displaying simulated x-rays as described. Reorientation module 666 on the server computing device 694 performs the hard work on the volumetric data, determining new volumetric data responsive to positional change data received from the client computing device and preparing and providing the simulated x-ray (a change image from a DRR) showing the positional change.

The GUI of the reorientation module 616 may be configured to receive the input through gestures applied over a display of an image providing graphical input such as by marking locations and/or drawing an axis, etc. Display device 606 may be a touch screen (or similar) input interface. Though shown as a laptop device, other form factors for client computing device 690 are contemplated. In another example paradigm, a single device may be configured rather than a client/server paradigm. The CT and other data and operations may be performed on the single device. The CT and other data may be stored remotely and accessed by the single device such that the server computing device may be a simplified data server. Though the client/server implementation may be configured using a native application on client computing device 690 rather than a browser based application.

In addition to computing device aspects, a person of ordinary skill will understand that computer program product aspects are disclosed, where instructions are stored in a non-transient storage device (e.g. a memory, CD-ROM, DVD-ROM, disc, etc.) to configure a computing device to perform any of the method aspects stored herein.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. A computer implemented method comprising, by a processing unit of a computing device:
  accessing a first volumetric data set of a medical image comprising anatomic structures;
  determining a volumetric region with respect to the first volumetric data set of an anatomic structure to be reoriented;
  computing a first measurement of a parameter of the anatomic structure;
  receiving a positional change of the volumetric region with respect to the first volumetric data set;

generating a second volumetric data set corresponding to the first volumetric data set and responsive to the positional change to the volumetric region;

generating a change image comprising a digitally reconstructed radiograph (DRR) from the second volumetric data set; wherein the DRR from the second volumetric data set is determined by updating a DRR from the first volumetric data set in only the region corresponding to the volumetric region for which the positional change is received; and providing the change image for display.

2. A computer implemented method comprising, by a processing unit of a computing device:

accessing a first volumetric data set of a medical image comprising anatomic structures;

determining a volumetric region with respect to the first volumetric data set of an anatomic structure to be reoriented;

computing a first measurement of a parameter of the anatomic structure;

receiving a positional change of the volumetric region with respect to the first volumetric data set;

generating a second volumetric data set corresponding to the first volumetric data set and responsive to the positional change to the volumetric region;

generating a change image comprising a digitally reconstructed radiograph (DRR) from the second volumetric data set;

providing the change image for display; and receiving a second or subsequent input defining a second or subsequent positional change and performing the steps of:

one of: a) updating the second volumetric data set responsive to the second or subsequent positional change; and b) generating a further volumetric data set responsive to the second or subsequent positional change;

generating an updated change image comprising a digitally reconstructed radiograph (DRR) from one of the second volumetric data set as updated and the further volumetric data set; and providing the updated change image;

thereby to iteratively perform reorientation of the anatomic structure.

3. The method of claim 2 wherein the anatomic structures comprise a hip joint.

4. The method of claim 2 wherein determining the volumetric region comprises receiving user input defining anatomic features as displayed on at least one slice view of the volumetric data set.

5. The method of claim 2 comprising:

generating a baseline image comprising a DRR from the first volumetric data set without regard to the positional change to the volumetric region; and providing the baseline image for display.

6. The method of claim 5 wherein the first measurement of a parameter is computed based on user input defining anatomic landmarks on the baseline image.

7. The method of claim 2 wherein the first measurement of a parameter is computed based on user input defining anatomic landmarks relative to the first volumetric data set.

8. The method of claim 2 wherein computing the first measurement computes the first measurement of a plurality of parameters.

9. The method of claim 2 wherein computing the first measurement of the parameter comprises computing one of: i) a lateral center edge angle (LCEA); ii) an anterior center edge angle (ACEA); and iii) both the LCEA and the ACEA.

10. The method of claim 2 wherein the positional change of the volumetric region and/or the second or subsequent positional change comprises one of:

a desired anteversion and/or inclination angle of an acetabulum;

a desired LCEA and/or ACEA;

a desired hip center of rotation location, and a value determined from a user manipulation receive via a user interface of the volumetric region using a computer input device in at least one slice view of one of the first, second or further volumetric data set, wherein the at least one slice view is displayed.

11. The method of claim 2 further comprising determining a second measurement of one or more parameters of the anatomic structure in the second volumetric data set and/or a further measurement of one or more parameters of the anatomic structure in the further volumetric data set.

12. The method of claim 11 wherein the second measurement of one or more parameters is based on a user input defining anatomic landmarks on either:

the DRR of the second volumetric data set; and a DRR of the first volumetric data set responsive to the positional change of the volumetric region.

13. The method of claim 11 wherein the further measurement of one or more parameters is based on a user input defining anatomic landmarks on either:

the DRR of the further volumetric data set; and the DRR of the second volumetric data set responsive to the second or subsequent positional change of the volumetric region.

14. The method of claim 11 comprising determining the positional change or the second or subsequent positional change to optimize the second measurement or the further measurement of the one or more parameters relative to respective desired values for the one or more parameters.

15. The method of claim 14 wherein determining the positional change comprises one of:

determining the positional change or the second or subsequent positional change automatically via an iterative algorithm; and receiving user input and presenting updated measurements of the one or more parameters to guide an iterative process.

16. The method of claim 2 further comprising generating navigation target parameters corresponding to the positional change or the second or subsequent positional change in a registration coordinate frame; wherein the navigation target parameters are transmitted to a surgical navigation system.

17. The method of claim 16 wherein the navigation target parameters comprises angles of inclination and anteversion of a hip joint.

18. A computing device comprising a processing unit and a storage unit coupled thereto, the storage unit storing instructions, which when executed by the processing unit, configure the computing device to:

access a first volumetric data set of a medical image comprising anatomic structures;

determine a volumetric region with respect to the first volumetric data set of an anatomic structure to be reoriented;

compute a first measurement of a parameter of the anatomic structure;

receive a positional change of the volumetric region with respect to the first volumetric data set;

generate a second volumetric data set corresponding to the first volumetric data set and responsive to the positional change to the volumetric region;

generate a change image comprising a digitally reconstructed radiograph (DRR) from the second volumetric data set;

provide the change image for display; and receive a second or subsequent input defining a second or subsequent positional change and performing the steps of:

one of: a) updating the second volumetric data set responsive to the second or subsequent positional change; and b) generating a further volumetric data set responsive to the second or subsequent positional change;

generating an updated change image comprising a DRR from one of the second volumetric data set as updated and the further volumetric data set; and providing the updated change image;

thereby to iteratively perform reorientation of the anatomic structure.

* * * * *